US012690892B2

(12) United States Patent  (10) Patent No.: US 12,690,892 B2
Du et al.  (45) Date of Patent: Jul. 28, 2026

(54) IN VIVO DEROTATION GROWTH-FRIENDLY SPINE IMPLANT SYSTEM

(71) Applicant: PEKING UNION MEDICAL COLLEGE AND CHINESE ACADEMY OF MEDICAL SCIENCES, Beijing (CN)

(72) Inventors: You Du, Beijing (CN); Shengru Wang, Beijing (CN); Jianguo Zhang, Beijing (CN); Bingtai Han, Beijing (CN); Yiwei Zhao, Beijing (CN); Haoran Zhang, Beijing (CN); Chenkai Li, Beijing (CN); Xiaohan Ye, Beijing (CN); Zhiyi Li, Beijing (CN)

(73) Assignee: PEKING UNION MEDICAL COLLEGE AND CHINESE ACADEMY OF MEDICAL SCIENCES, Beijing (CN)

( * ) Notice: Subject to any disclaimer, the term of this patent is extended or adjusted under 35 U.S.C. 154(b) by 46 days.

(21) Appl. No.: 18/835,851

(22) PCT Filed: Mar. 28, 2024

(86) PCT No.: PCT/CN2024/084382
§ 371 (c)(1),
(2) Date: Aug. 5, 2024

(87) PCT Pub. No.: WO2025/086546
PCT Pub. Date: May 1, 2025

(65) Prior Publication Data
US 2026/0000433 A1  Jan. 1, 2026

(30) Foreign Application Priority Data
Oct. 25, 2023  (CN) .......................... 202311387129.8

(51) Int. Cl.
*A61B 17/70* (2006.01)

(52) U.S. Cl.
CPC ................................ *A61B 17/7002* (2013.01)

(58) Field of Classification Search
CPC ............ A61B 17/7002; A61B 17/7008; A61B 17/7014; A61B 17/7019; A61B 17/702; A61B 17/7028
(Continued)

(56) References Cited

U.S. PATENT DOCUMENTS 8,114,133 B2 * 2/2012 Logan ................ A61B 17/7032
606/258
8,226,690 B2 * 7/2012 Altarac .............. A61B 17/7017
606/256
(Continued)

FOREIGN PATENT DOCUMENTS

CN    2920174 Y    7/2007
CN    202821566 U    3/2013
(Continued)

*Primary Examiner* — Eduardo C Robert
*Assistant Examiner* — Christina Negrellirodriguez
(74) *Attorney, Agent, or Firm* — NKL Law; Allen Xue

(57) ABSTRACT

An in vivo derotation growth-friendly spine implant system includes: a rod; first fixing units arranged at both ends of the rod, respectively; and a twisting assembly comprising a second fixing unit and a rotating assembly. The rotating assembly wraps an outer side of the rod; the second fixing unit is arranged in a middle part of the rotating assembly, and the two are detachably connected; both ends of the rotating assembly are connected to the rod; the rotating assembly comprises a connecting ring, a connecting block, a first twisting unit, and a second twisting unit. The rotating assembly is connected to a spine through the second fixing unit, a twisting force is applied to the rotating assembly, and a strong anti-rotating force is applied to a vertebral body (Continued)

through the second fixing unit, such that the rotation of the vertebral body is corrected, and thus scoliosis is corrected.

17 Claims, 8 Drawing Sheets

(58) Field of Classification Search
USPC .................................................. 606/257–259
See application file for complete search history.

(56) References Cited

U.S. PATENT DOCUMENTS

| | | | |
|---|---|---|---|
| 8,361,118 B2 * | 1/2013 | Biedermann | ........ A61B 17/702 |
| | | | 606/259 |
| 2008/0300633 A1 * | 12/2008 | Jackson | ............. A61B 17/7011 |
| | | | 606/301 |
| 2010/0174318 A1 | 7/2010 | Ritland | |
| 2013/0144341 A1 * | 6/2013 | Jackson | ............. A61B 17/7028 |
| | | | 606/257 |
| 2015/0119939 A1 * | 4/2015 | Frey | ................... A61B 17/7031 |
| | | | 606/258 |
| 2015/0342646 A1 | 12/2015 | Wessels et al. | |

FOREIGN PATENT DOCUMENTS

| | | | |
|---|---|---|---|
| CN | 205569056 U | 9/2016 |
| CN | 208447754 U | 2/2019 |
| CN | 208958295 U | 6/2019 |
| CN | 213465279 U | 6/2021 |
| CN | 113367785 A | 9/2021 |
| CN | 113827330 A | 12/2021 |
| CN | 115670622 A | 2/2023 |
| CN | 219147853 U | 6/2023 |

* cited by examiner

33

1

31

34

32

IN VIVO DEROTATION GROWTH-FRIENDLY SPINE IMPLANT SYSTEM

CROSS REFERENCE OF RELATED APPLICATIONS

This application is a U.S. national stage entry of PCT International Application No. PCT/CN2024/084382, filed on Mar. 28, 2024 which claims priority to the Chinese Patent Application No. 202311387129.8 entitled "IN VIVO DEROTATION GROWTH-FRIENDLY SPINE IMPLANT SYSTEM" and filed on Oct. 25, 2023, the content of which is incorporated herein by reference in its entirety.

The present application claims priority to the Chinese Patent Application No. 202311387129.8 entitled "IN VIVO DEROTATION GROWTH-FRIENDLY SPINE IMPLANT SYSTEM" and filed on Oct. 25, 2023.

TECHNICAL FIELD

The present invention belongs to the technical field of medical instruments, and in particular, relates to a spine implant device.

BACKGROUND

Early-onset scoliosis (EOS) refers to a spine deformity diagnosed before the age of 10 in children. In order to achieve the purpose of controlling the spine deformity while reserving the growth potential of the spine and the thorax, an orthopedic surgery using a growth-friendly spine implant is required.

The growth-friendly spine implant can correct the spine deformity while reserving the spinal growth potential to promote spinal growth. For a spine with scoliosis deformity, the vertebrae usually have both a coronal plane translational deformity and an axial plane rotational deformity. For the coronal plane translational deformity of the vertebrae, a growth-friendly spine implant capable of longitudinal distraction can provide a longitudinal traction force through distraction to correct the coronal plane translational deformity. However, for the axial rotational deformity of the vertebrae, the longitudinal traction force provided through distraction is very limited for rotational deformity correction and is not easily maintained. Therefore, the existing growth-friendly spine implants cannot meet the derotation requirements for the rotational deformity of the vertebrae.

In response to the above problems, the present invention provides an in vivo derotation growth-friendly spine implant system.

SUMMARY

To overcome the problem put forward in the background, the present invention provides an in vivo derotation growth-friendly spine implant system.

Provided is an in vivo derotation growth-friendly spine implant system, comprising:

a rod;

first fixing units arranged at both ends of the rod, respectively; and a twisting assembly comprising a second fixing unit and a rotating assembly, wherein the rotating assembly wraps an outer side of the rod, the second fixing unit is arranged in a middle part of the rotating assembly, and the two are detachably connected; both ends of the rotating assembly are connected to the rod.

Further, end caps are arranged at both ends of the rotating assembly, respectively; the end caps are adapted to the rod.

Further, the rotating assembly comprises a connecting ring, a connecting block, a first twisting unit, and a second twisting unit; the connecting block is arranged between the first twisting unit and the second twisting unit; one end of the connecting ring is adapted to the connecting block, and the other end is adapted to the second fixing unit.

Further, the second fixing unit comprises a second fixing bolt, a second locking bolt, a buttress, and a second mounting part; the second fixing bolt is fixedly connected to the second mounting part; one end of the second locking bolt is threadedly connected to the second mounting part, and the other end is threadedly connected to the buttress after penetrating through the connecting ring.

Further, the second fixing unit comprises a second fixing bolt and a second mounting part; the second fixing bolt is fixedly connected to the second mounting part; one end of the second fixing bolt away from the second mounting part is connected to a spine of a patient after penetrating through the connecting ring.

Further, the rod comprises a first fixing end, a connecting part, and a second fixing end; the connecting part is arranged between the first fixing end and the second fixing end, and the three are fixedly connected; the first fixing units are connected to the first fixing end and the second fixing end, respectively.

Further, the rod further comprises a first force-bearing part and a second force-bearing part; the first force-bearing part is arranged between the first fixing end and the connecting part; the second force-bearing part is arranged between the second fixing end and the connecting part; the end caps are adapted to the first force-bearing part and the second force-bearing part, respectively.

Further, each of the first fixing units comprises a first mounting part, a first fixing bolt, a first locking bolt, and an anti-twisting structure; one end of the first fixing bolt is an expansion end; the expansion end is stuck in the first mounting part; the anti-twisting structure is arranged in the first mounting part; an inner wall of the anti-twisting structure is adapted to each of the first fixing end and the second fixing end; the first locking bolt is threadedly connected to the first mounting part; the first locking bolt presses the rod in the anti-twisting structure, and the first locking bolt presses the anti-twisting structure in the first mounting part.

Further, one end of the rod is provided with a connecting structure and an extending rod; the extending rod is connected to the rod through the connecting structure; one end of the extending rod away from the rod is provided with third fixing units; the third fixing units are separated from the extending rod and fixed on a side wall of the extending rod.

Further, each of the third fixing units comprises a third fixing bolt, a third locking bolt, and a third mounting part; the third mounting part is fixedly connected to the third fixing bolt; the third locking bolt is threadedly connected to the third mounting part; the third locking bolt presses the extending rod against an inner side wall of the third mounting part, and a friction force is applied to lock a relative position relationship between the extending rod and the third fixing unit.

The present invention has the following beneficial effects: The rotating assembly is connected to a spine through the second fixing unit, a twisting force is applied to the rotating assembly, and a strong anti-rotating force is applied to the vertebral body through the second fixing unit, such that the rotation of the vertebral body is corrected, and thus scoliosis is corrected.

Figure 1:
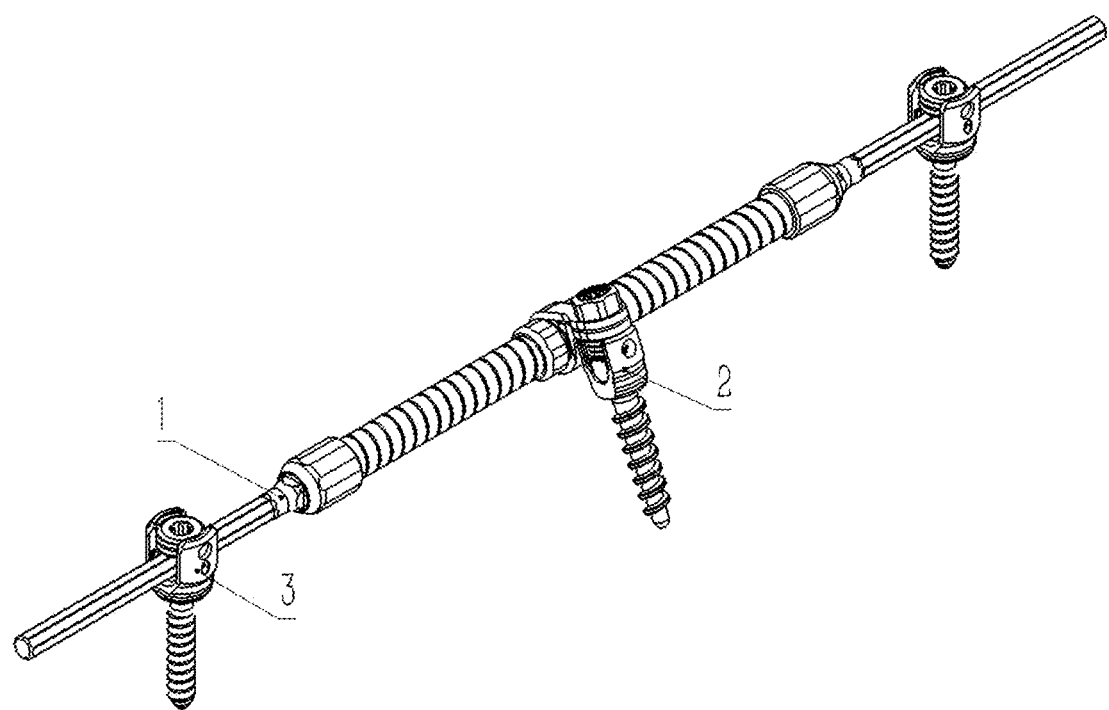
FIG. 1 is a schematic structural diagram of an in vivo derotation growth-friendly spine implant system implementing the present invention.
Figure 2:
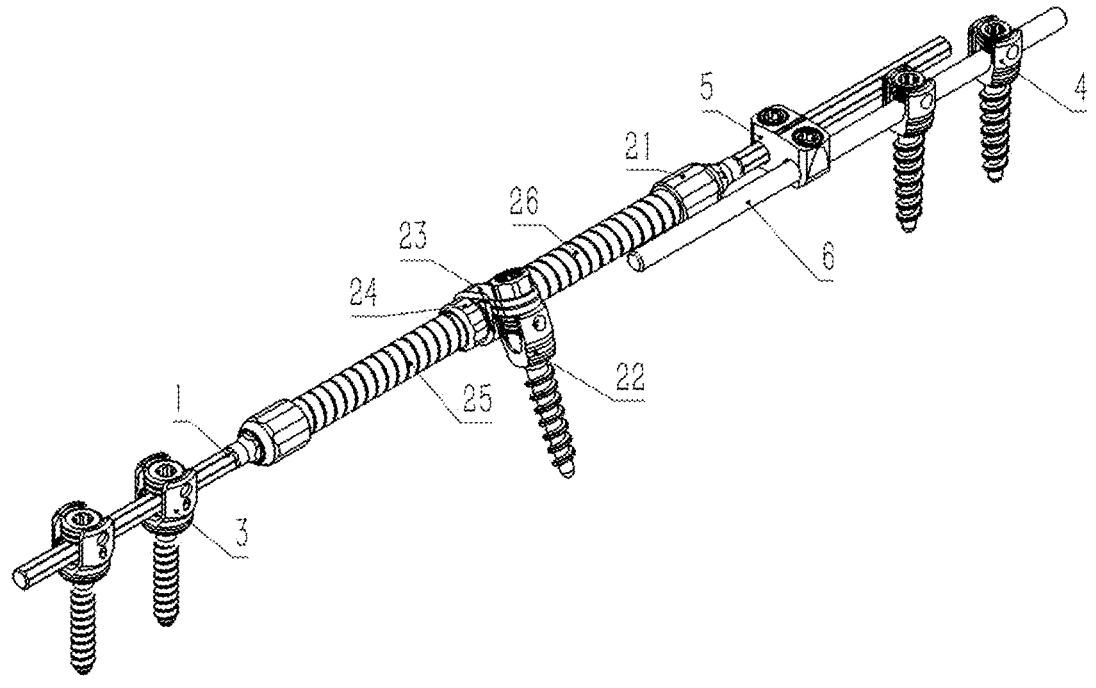
FIG. 2 is a schematic structural diagram of another in vivo derotation growth-friendly spine implant system implementing the present invention.
Figure 3:
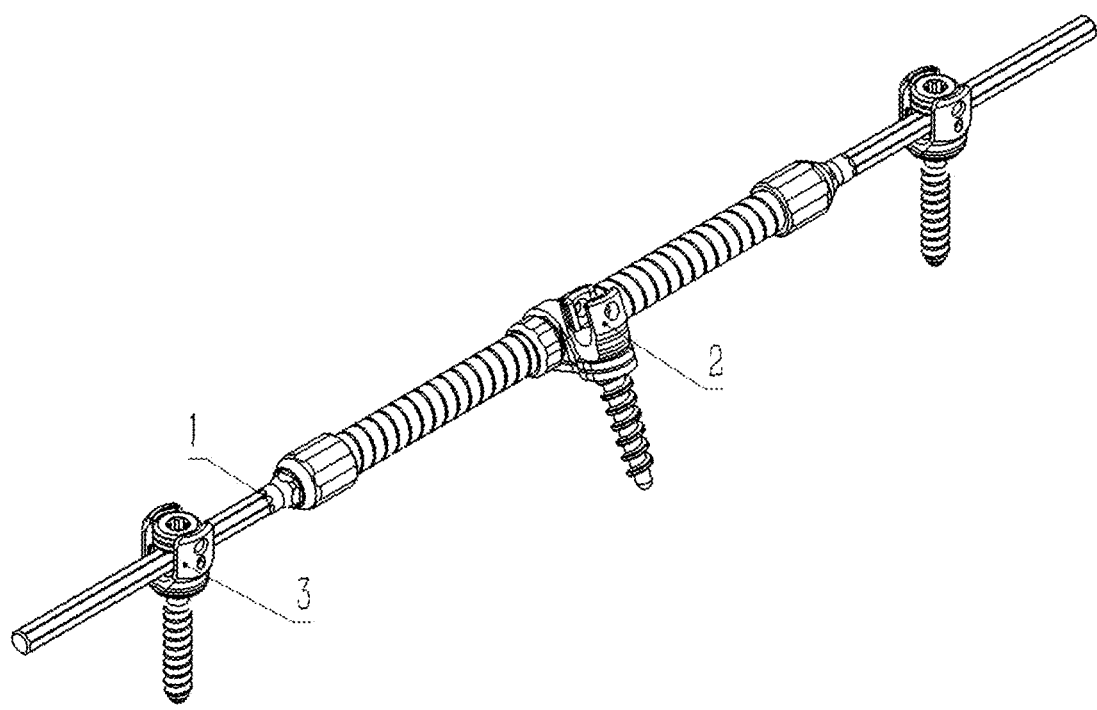
FIG. 3 is a schematic structural diagram of a third in vivo derotation growth-friendly spine implant system implementing the present invention.
Figure 4:
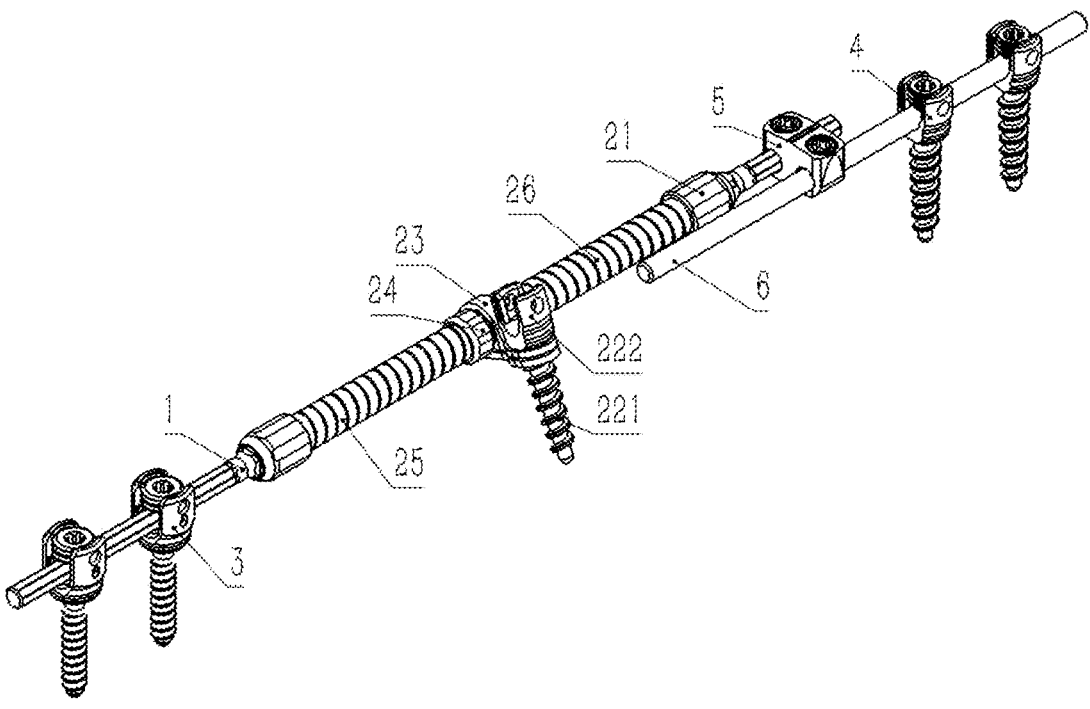
FIG. 4 is a schematic structural diagram of a fourth in vivo derotation growth-friendly spine implant system implementing the present invention.

In the figures, 1: rod; 2: twisting assembly; 3: first fixing unit; 4: third fixing unit; 5: connecting structure; 6: extending rod; 11: first fixing end; 12: first force-bearing part; 13: connecting part; 14: second force-bearing part; 15: second fixing end; 21: end cap; 22: second fixing unit; 23: connecting ring; 24: connecting block; 25: first twisting unit; 26: second twisting unit; 31: first mounting part; 32: first fixing bolt; 33: first locking bolt; 34: anti-twisting structure; 41: third fixing bolt; 42: third locking bolt; 51: connecting support; 52: limiting bolt; 221: second fixing bolt; 222: pressing block; 223: second locking bolt; and 224: buttress.

DETAILED DESCRIPTION

The technical solutions in embodiments of the present invention will be clearly and completely described below with reference to the drawings in the embodiments of the present invention. It is obvious that the described embodiments are only part of the embodiments of the present invention rather than all of the embodiments. The present invention can also be implemented or applied by other different specific embodiments. The following embodiments and features in the embodiments can be combined with each other without conflict. Based on the embodiments of the present invention, all other embodiments obtained by those of ordinary skills in the art without creative work shall fall within the protection scope of the present invention.

In the description of the present invention, it should be understood that the terms such as "up", "down", "front", "rear", "bottom", "inner", "outer", "clockwise", "counterclockwise", and other directional or positional indications are based on the directions or position shown in the drawings. These terms are merely intended to facilitate and simplify the description of the present invention, rather than to indicate or imply that the indicated equipment or element must have a specific direction and be structured and operated according to the specific direction. Therefore, these terms should not be construed as limiting the present invention.

Furthermore, the terms "first" and "second" are only for the purpose of description, and may not be construed as indicating or implying the relative importance or implicitly indicating the number of the indicated technical features. Thus, features defined by "first" and "second" may explicitly or implicitly include one or more of the features. In the description of the present invention, "plurality" refers to two or more, unless otherwise explicitly and specifically defined.

Embodiment 1

Provided is an in vivo derotation growth-friendly spine implant system, as shown in FIGS. 1-11, comprising:

a rod 1;

first fixing units 3 arranged at both ends of the rod 1, respectively, the first fixing units 3 being connected to the rod 1; and a twisting assembly 2 comprising a second fixing unit 22 and a rotating assembly (not identified in the figures), wherein the rotating assembly wraps an outer side of the rod 1, the second fixing unit 22 is arranged in a middle part of the rotating assembly, and the two are detachably connected; both ends of the rotating assembly are connected to the rod 1.

In use, the first fixing units 3 are fixed at both ends of a scoliotic portion of a patient, and the rod 1 is mounted in the first fixing units 3; after applying a twisting force to the rotating assembly, the second fixing unit 22 is then fixed at a position with the heaviest rotational deformity in the apical vertebra of scoliosis. In this case, the rotating assembly gradually releases the carried twisting force, and the position with the heaviest rotational deformity in the apical vertebra of scoliosis is driven through the second fixing unit 22 to gradually rotate, such that the spine gradually restores to a normal state.

End caps 21 are arranged at both ends of the rotating assembly, respectively; the end caps 21 are adapted to the rod 1.

Specifically, a polygonal through hole is formed in each of the end caps 21, and a first force-bearing part 12 and a second force-bearing part 14 adapted to the end caps 21 are arranged on the rod 1. Both ends of the rotating assembly are connected to the rod 1 through the end caps 21 to prevent the rotating assembly and the rod 1 from rotating relatively and to stop the additional consumption of the twisting force carried by the rotating assembly, so as to ensure that the twisting force carried by the rotating assembly can be completely released to the position with the heaviest rotational deformity in the apical vertebra of scoliosis through the second fixing unit 22, thereby ensuring the therapeutic effect.

Further, a square through hole is formed in each of the end caps 21.

Figure 5:
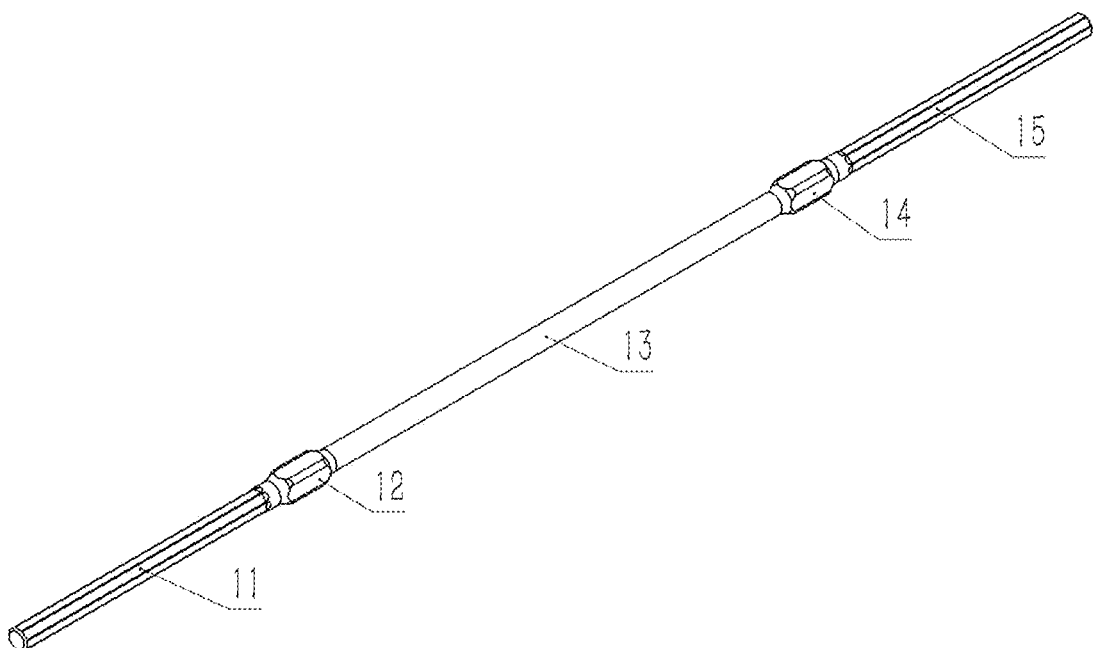
FIG. 5 is a schematic structural diagram of a rod implementing the present invention.
Figure 6:
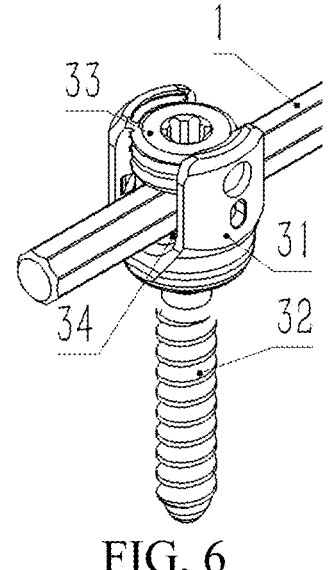
FIG. 6 is a schematic diagram illustrating the mounting of a first fixing unit and the rod implementing the present invention.
Figure 7:
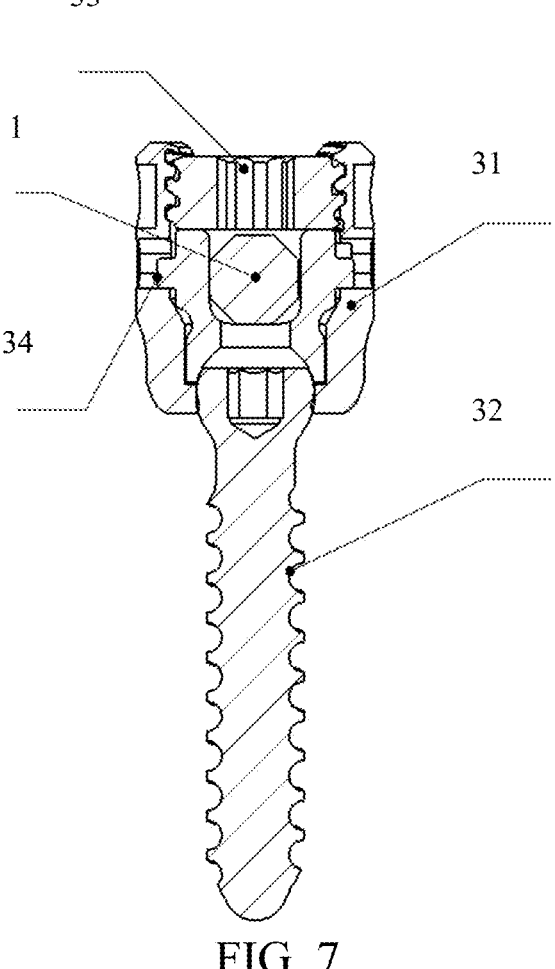
FIG. 7 is a cross-sectional diagram of the first fixing unit implementing the present invention.

As shown in FIG. 5, the rod 1 comprises a first fixing end 11, a connecting part 13, and a second fixing end 15; the connecting part 13 is arranged between the first fixing end 11 and the second fixing end 15, and the three are fixedly connected; the first fixing units 3 are connected to the first fixing end 11 and the second fixing end 15, respectively.

Each of the first fixing units 3 comprises a first mounting part 31, a first fixing bolt 32, a first locking bolt 33, and an anti-twisting structure 34; one end of the first fixing bolt 32 is an expansion end; the expansion end is stuck in the first mounting part 31; the anti-twisting structure 34 is arranged in the first mounting part 31; an inner wall of the anti-twisting structure 34 is adapted to each of the first fixing end 11 and the second fixing end 15; the first locking bolt 33 is threadedly connected to the first mounting part 31; the first locking bolt 33 presses the rod 1 in the anti-twisting structure 34, the first locking bolt 33 presses the anti-twisting structure 34 in the first mounting part 31, and a friction force is applied to lock the relative position relationship between the rod 1 and the first fixing unit 3.

The rod 1 further comprises a first force-bearing part 12 and a second force-bearing part 14; the first force-bearing part 12 is arranged between the first fixing end 11 and the connecting part 13; the second force-bearing part 14 is arranged between the second fixing end 15 and the connecting part 13; the end caps 21 are adapted to the first force-bearing part 12 and the second force-bearing part 14, respectively.

Specifically, the first force-bearing part 12 and the second force-bearing part 14 are both square prisms adapted to the end caps 21. In this case, the rod 1 and the end caps 21 do not rotate relatively in use.

As can be seen with reference to FIGS. 1-11, the first fixing end 11 and the second fixing end 15 are regular octagonal prisms. A square through hole is formed in the anti-twisting structure 34. The regular octagonal prisms are fitted with the square through hole in the anti-twisting structure 34 to prevent the rod 1 and the first fixing units 3 from rotating relatively. After the first fixing units 3 are implanted into the spine of the patient, no rotation exists between the rod 1 and the first fixing units 3, and no rotation exists between the rod 1 and the end caps 21, such that the twisting force carried by the rotating assembly can be completely applied to the position with the heaviest rotational deformity in the apical vertebra of scoliosis through the second fixing unit 22, thereby enhancing the therapeutic effect.

As can be seen in FIGS. 1-11, the rotating assembly comprises a connecting ring 23, a connecting block 24, a first twisting unit 25, and a second twisting unit 26; the connecting block 24 is arranged between the first twisting unit 25 and the second twisting unit 26; one end of the connecting ring 23 is adapted to the connecting block 24, and the other end is adapted to the second fixing unit 22. Specifically, the first twisting unit 25 and the second twisting unit 26 are torsion springs with opposite rotation directions. The first twisting unit 25 is a torsion spring with a clockwise rotation direction, and the second twisting unit 26 is a torsion spring with a counterclockwise rotation direction. Alternatively, the first twisting unit 25 is a torsion spring with a counterclockwise rotation direction, and the second twisting unit 26 is a torsion spring with a clockwise rotation direction.

One end of each of the torsion springs is connected to one of the end caps 21, and the other end is connected to the connecting block 24. One end of each of the torsion springs is connected to the rod 1 through one of the end caps 21, and the end caps 21 are adapted to the rod 1, such that the torsion springs are prevented from releasing the carried twisting forces at ends facing the end caps 21.

Both ends of the connecting block 24 are connected to the first twisting unit 25 and the second twisting unit 26, respectively, a middle part of the connecting block 24 is connected to the connecting ring 23, and an inner part of the connecting block 24 is rotatably connected to the rod 1. The twisting forces carried by the torsion springs are enabled to be transmitted to the connecting ring 23 through the connecting block 24 and then transmitted to the position with the heaviest rotational deformity in the apical vertebra of scoliosis through the second fixing unit 22, thereby driving the spine of the patient to gradually restore to the normal state.

Specifically, an opening capable of opening to deform is formed in the connecting ring 23 to facilitate the mounting and detachment between the connecting ring 23 and the connecting block 24. In use, the second fixing unit 22 tightly presses the opening in the connecting ring 23 to lock the relative position relationship between the connecting ring 23 and the connecting block 24. One end of the connecting ring 23 wraps an outer part of the connecting block 24. The part of the connecting block 24 in contact with the connecting ring 23 is a hollow regular hexadecagonal prism, and the part of the connecting ring 23 in contact with the block is a regular octagonal through hole. The regular hexadecagonal prism is fitted with the regular octagonal through hole, such that the connecting ring 23 and the connecting block 24 are prevented from rotating relatively, while the connecting angle range of the connecting ring 23 and the connecting block 24 is increased, thereby improving the applicability of the twisting assembly 2 to meet the requirements of different patients. The second fixing unit 22 comprises a second fixing bolt 221, a second locking bolt 223, a buttress 224, and a second mounting part (not identified in the figures); the second fixing bolt 221 is fixedly connected to the second mounting part; one end of the second locking bolt 223 is threadedly connected to the second mounting part, and the other end is threadedly connected to the buttress 224 after penetrating through the connecting ring 23.

In the embodiments of the present application, the second fixing unit 22 further comprises a pressing block 222. The pressing block 222 is arranged in the second mounting part and is located at one end of the second locking bolt 223 away from the buttress 224. The pressing block 222 is rotatably connected to the second locking bolt 223. After the second locking bolt 223 is screwed up in the second mounting part, the pressing block 222 is pressed, and the pressing block 222 then produces a reaction force to the second locking bolt 223, such that threads on the second locking bolt 223 tightly abut against threads in the second mounting part to strengthen the connection stability between the second locking bolt 223 and the second mounting part, thereby effectively preventing the second locking bolt 223 from rotating unexpectedly.

In use, one end of the second fixing bolt 221 away from the second mounting part is threadedly connected to the spine of the patient. After one end of the second locking bolt 223 is screwed into one end of the second mounting part away from the second fixing bolt 221, the second locking bolt 223 penetrates through one end of the connecting ring 23 away from the connecting block 24, and then the buttress 224 is screwed up to tightly press the opening in the connecting ring 23, such that the relative position relationship between the connecting ring 23 and the connecting block 24 is locked; meanwhile, the connecting ring 23 is fixed between the buttress 224 and the second mounting part, such that the relative position relationship between the connecting ring 23 and the second fixing unit 22 is locked, and thus the twisting force carried by the rotating assembly can be completely applied to the position with the heaviest rotational deformity in the apical vertebra of scoliosis.

The working principle of the embodiment is as follows:

The first fixing bolts 32 are mounted at both ends of the scoliotic part of the patient, respectively, the second fixing bolt 221 is mounted at the position with the heaviest rotational deformity in the apical vertebra of scoliosis, the second fixing bolt 221, under the drive of the first twisting unit 25 and the second twisting unit 26, rotates by taking the axis of the rod 1 as the axial core, and the portion with the heaviest rotational deformity in the apical vertebra of scoliosis is driven to rotate, such that partial vertebrae of scoliosis gradually restore to the normal state.

The use method of the embodiment is as follows:

1. A plurality of the first fixing bolts 32 are mounted at both ends of the scoliotic part of the patient.
2. The second fixing bolt 221 is mounted at the position with the heaviest rotational deformity in the apical vertebra of scoliosis.
3. The rotating assembly and the end caps 21 are mounted at the outer side of the rod 1.
4. The anti-twisting structure 34 and the rod 1 are mounted in the first mounting part 31 and locked by using the first locking bolt 33.
5. The pressing block 222 and the second locking bolt 223 are mounted in the second mounting part; the second locking bolt 223 is screwed up.
6. Twisting forces are applied to the first twisting unit 25 and the second twisting unit 26.
7. One end of the connecting ring 23 away from the connecting block 24 is mounted on the second locking bolt 223 and locked by using the buttress 224.

Embodiment 2

As shown in FIGS. 2-11, this embodiment is different from Embodiment 1 in that:

One end of the rod 1 is provided with a connecting structure 5 and an extending rod 6; the extending rod 6 is connected to the rod 1 through the connecting structure 5; one end of the extending rod 6 away from the rod 1 is provided with third fixing units 4; the third fixing units 4 are separated from the extending rod 6 and fixed on the side wall of the extending rod 6.

Specifically, the connecting structure 5 comprises a connecting support 51 and limiting bolts 52. Two parallel through holes (not identified in the figures) and two threaded holes (not identified in the figures) perpendicular to the through holes are formed in the connecting support 51. The rod 1 and the extending rod 6 are both adapted to the through holes. The limiting bolts 52 are both adapted to the threaded holes. In use, the rod 1 and the extending rod 6 penetrate through the connecting support 51 via the two through holes, respectively, then the limiting bolts 52 are screwed into the threaded holes, and the limiting bolts 52 are enabled to be in contact with the side walls of the rod 1 and the extending rod 6, respectively, thereby pressing the rod 1 and the extending rod 6 against the side walls of the through holes. A friction force is applied to lock the position relationship between the rod 1 and the connecting structure 5, and a friction force is also applied to lock the position relationship between the extending rod 6 and the connecting structure 5, thereby locking the position relationship between the rod 1 and the extending rod 6.

Specifically, the bottom of the limiting bolts 52 is a plane, and when the limiting bolts 52 are in contact with the rod 1, the bottom of the limiting bolts 52 is in surface contact with the first fixing end 11 or the second fixing end 15, such that the rod 1 and the connecting structure 5 are prevented from rotating relatively.

Figure 8:
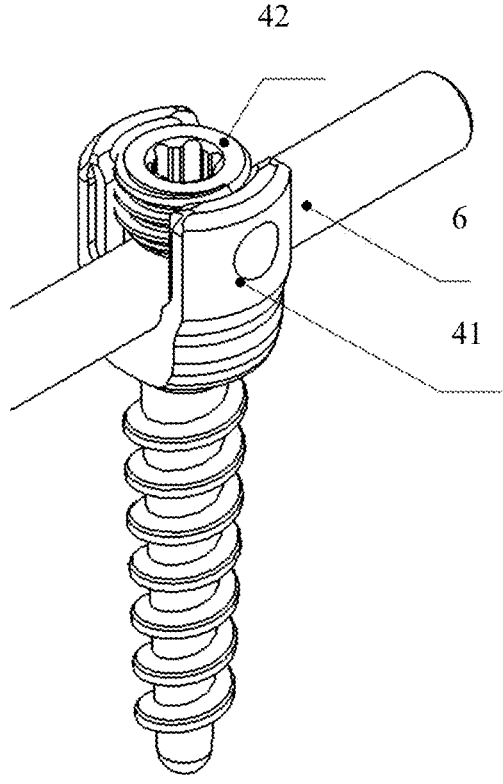
FIG. 8 is a schematic diagram illustrating the mounting of a third fixing unit and an extending rod implementing the present invention.
Figure 9:
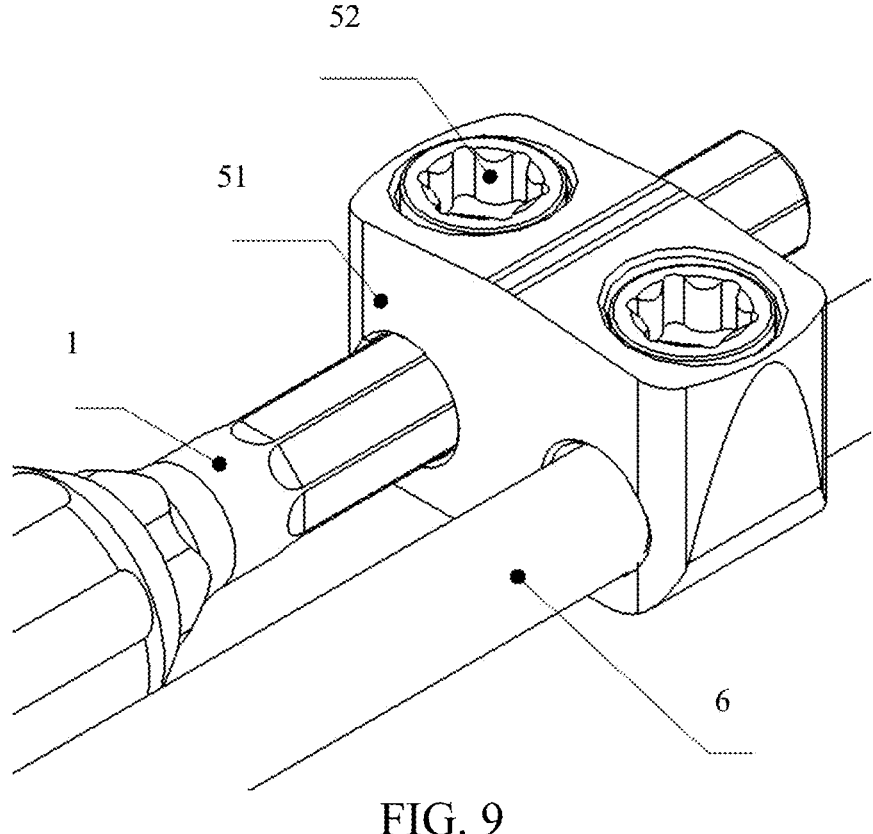
FIG. 9 is a schematic diagram illustrating the mounting of a connecting structure, the rod and the extending rod implementing the present invention.
Figure 10:
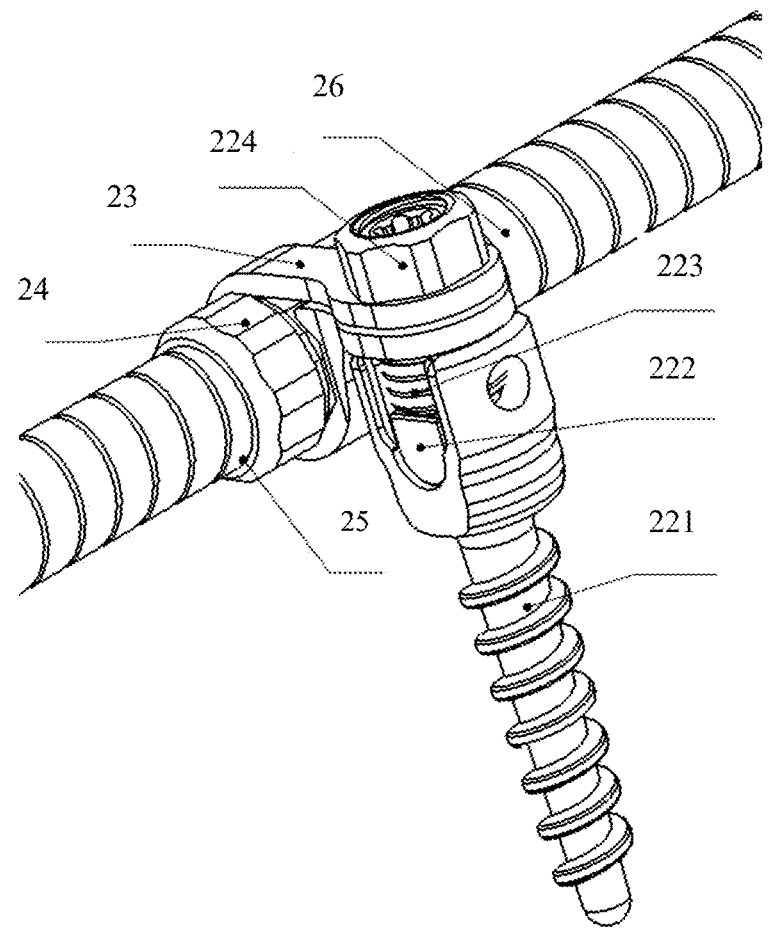
FIG. 10 is a schematic diagram illustrating the mounting of a second fixing unit, a connecting ring and a connecting block implementing the present invention.
Figure 11:
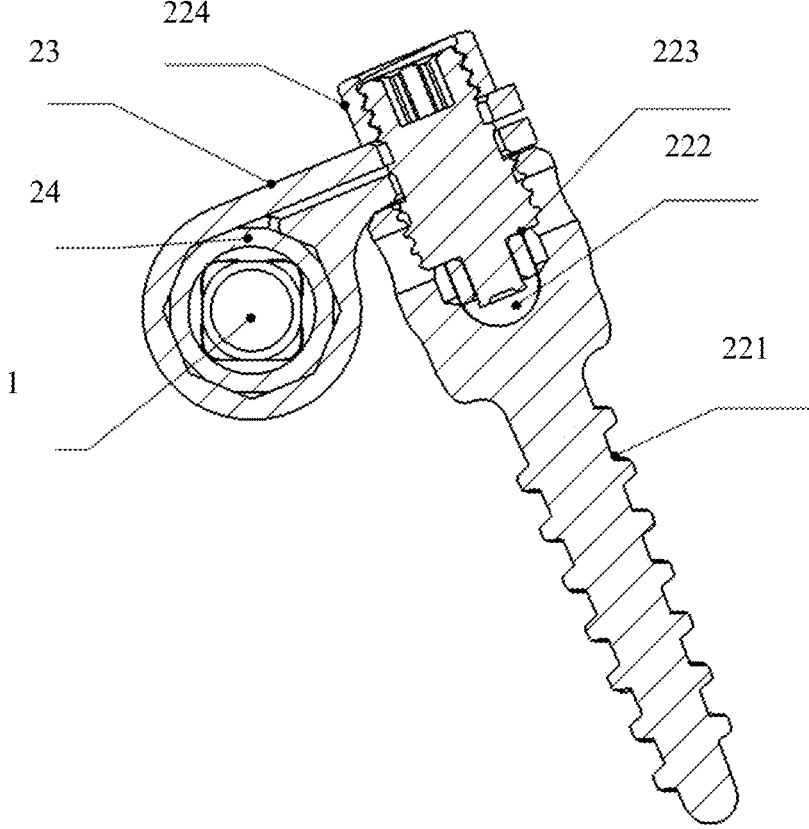
FIG. 11 is a cross-sectional diagram of the second fixing unit implementing the present invention.

As shown in FIG. 8, each of the third fixing units 4 comprises a third fixing bolt 41, a third locking bolt 42, and a third mounting part (not identified in the figure); the third mounting part is fixedly connected to the third fixing bolt 41; the third locking bolt 42 is threadedly connected to the third mounting part; the third locking bolt 42 presses the extending rod 6 against the inner side wall of the third mounting part, and a friction force is applied to lock the relative position relationship between the extending rod 6 and the third fixing unit 4.

The use method of the embodiment is as follows:

1. A plurality of the first fixing bolts 32 are mounted at both ends of the scoliotic part of the patient.
2. The second fixing bolt 221 is mounted at the position with the heaviest rotational deformity in the apical vertebra of scoliosis.
3. A plurality of the third fixing bolts 41 are mounted at appropriate positions.
4. The rotating assembly and the end caps 21 are mounted at the outer side of the rod 1.
5. The anti-twisting structure 34 and the rod 1 are mounted in the first mounting part 31 and locked by using the first locking bolt 33.
6. The extending rod 6 is mounted in the third mounting part and locked by using the third locking bolt 42.
7. The pressing block 222 and the second locking bolt 223 are mounted in the second mounting part; the second locking bolt 223 is screwed up.
8. Twisting forces are applied to the first twisting unit 25 and the second twisting unit 26.
9. One end of the connecting ring 23 away from the connecting block 24 is mounted on the second locking bolt 223 and locked by using the buttress 224.

Embodiment 3

As shown in FIGS. 3-11, this embodiment is different from Embodiments 1 and 2 in that:

The second fixing unit 22 comprises a second fixing bolt 221 and a second mounting part; the second fixing bolt 221 is fixedly connected to the second mounting part; one end of the second fixing bolt 221 away from the second mounting part is connected to the spine of the patient after penetrating through the connecting ring 23.

After the second fixing bolt 221 penetrates through one end of the connecting ring 23 away from the connecting block 24 and is then implanted into the position with the heaviest rotational deformity in the apical vertebra of scoliosis, the opening in the connecting ring 23 is pressed tightly, such that the relative position relationship between the connecting ring 23 and the connecting block 24 is locked; meanwhile, the connecting ring 23 is fixed between the second mounting part and the spine of the patient, such that the relative position relationship between the connecting ring 23 and the second fixing unit 22 is locked, and thus the twisting force carried by the rotating assembly can be completely applied to the position with the heaviest rotational deformity in the apical vertebra of scoliosis of the patient.

The use method of the embodiment is as follows:

1. A plurality of the first fixing bolts 32 are mounted at both ends of the scoliotic part of the patient.
2. The rotating assembly and the end caps 21 are mounted at the outer side of the rod 1.

3. The anti-twisting structure 34 and the rod 1 are mounted in the first mounting part 31 and locked by using the first locking bolt 33.

4. Twisting forces are applied to the first twisting unit 25 and the second twisting unit 26.

6. The second fixing bolt 221 penetrates through one end of the connecting ring 23 away from the connecting block 24 and is then mounted at the position with the heaviest rotational deformity in the apical vertebra of scoliosis.

Alternatively, the use method of the embodiment is as follows:

1. A plurality of the first fixing bolts 32 are mounted at both ends of the scoliotic part of the patient.

2. A plurality of the third fixing bolts 41 are mounted at appropriate positions.

3. The rotating assembly and the end caps 21 are mounted at the outer side of the rod 1.

4. The anti-twisting structure 34 and the rod 1 are mounted in the first mounting part 31 and locked by using the first locking bolt 33.

5. The extending rod 6 is mounted in the third mounting part and locked by using the third locking bolt 42.

6. Twisting forces are applied to the first twisting unit 25 and the second twisting unit 26.

7. The second locking bolt 223 penetrates through one end of the connecting ring 23 away from the connecting block 24 and is mounted at the position with the heaviest rotational deformity in the apical vertebra of scoliosis.

The basic principles, main features, and advantages of the present invention have been shown and described above. It should be understood by those skilled in the art that the present invention is not limited to the above embodiments, and the above embodiments and embodiments described in the specification are only preferred embodiments of the present invention and are not intended to limit the present invention. Without departing from the spirit and scope of the present invention, various changes and improvements can be made to the present invention, and these changes and improvements fall within the scope of the invention claimed. The scope of the present invention is defined by the appended claims and equivalents thereof.

The invention claimed is:

1. An in vivo derotation growth-friendly spine implant system, comprising:

a rod;

first fixing units arranged at both ends of the rod, respectively; and a twisting assembly comprising a second fixing unit and a rotating assembly, wherein the rotating assembly wraps an outer side of the rod; the second fixing unit is arranged in a middle part of the rotating assembly, and the second fixing unit and the rotating assembly are detachably connected; both ends of the rotating assembly are connected to the rod; the rotating assembly comprises a connecting ring, a connecting block, a first twisting unit, and a second twisting unit; the connecting block is arranged between the first twisting unit and the second twisting unit; one end of the connecting ring is adapted to the connecting block, and the other end is adapted to the second fixing unit; the first twisting unit and the second twisting unit are torsion springs with opposite rotation directions;

wherein the second fixing unit comprises a second fixing bolt, a second locking bolt, a buttress, and a second mounting part; the second fixing bolt is fixedly connected to the second mounting part; one end of the second locking bolt is threadedly connected to the second mounting part, and the other end is threadedly connected to the buttress after penetrating through the connecting ring; or wherein the second fixing unit comprises a second fixing bolt and a second mounting part; the second fixing bolt is fixedly connected to the second mounting part; one end of the second fixing bolt away from the second mounting part is adapted to be connected to a spine of a patient after penetrating through the connecting ring.

2. The in vivo derotation growth-friendly spine implant system according to claim 1, wherein end caps are arranged at both ends of the rotating assembly, respectively; the end caps are adapted to the rod.

3. The in vivo derotation growth-friendly spine implant system according to claim 2, wherein the rod comprises a first fixing end, a connecting part, and a second fixing end; the connecting part is arranged between the first fixing end and the second fixing end, and the first fixing end, the connecting part, and the second fixing end are fixedly connected; the first fixing units are connected to the first fixing end and the second fixing end, respectively.

4. The in vivo derotation growth-friendly spine implant system according to claim 2, wherein one end of the rod is provided with a connecting structure and an extending rod; the extending rod is connected to the rod through the connecting structure; one end of the extending rod away from the rod is provided with third fixing units; the third fixing units are separated from the extending rod and fixed on a side wall of the extending rod.

5. The in vivo derotation growth-friendly spine implant system according to claim 3, wherein the rod further comprises a first force-bearing part and a second force-bearing part; the first force-bearing part is arranged between the first fixing end and the connecting part; the second force-bearing part is arranged between the second fixing end and the connecting part; the first force-bearing part and the second force-bearing part are both adapted to the end caps.

6. The in vivo derotation growth-friendly spine implant system according to claim 3, wherein each of the first fixing units comprises a first mounting part, a first fixing bolt, a first locking bolt, and an anti-twisting structure; one end of the first fixing bolt is an expansion end; the expansion end is stuck in the first mounting part; the anti-twisting structure is arranged in the first mounting part; an inner wall of the anti-twisting structure is adapted to each of the first fixing end and the second fixing end; the first locking bolt is threadedly connected to the first mounting part; the first locking bolt presses the rod in the anti-twisting structure, and the first locking bolt presses the anti-twisting structure in the first mounting part.

7. The in vivo derotation growth-friendly spine implant system according to claim 3, wherein the second fixing end of the rod is provided with a connecting structure and an extending rod; the extending rod is connected to the rod through the connecting structure; one end of the extending rod away from the rod is provided with third fixing units; the third fixing units are separated from the extending rod and fixed on a side wall of the extending rod.

8. The in vivo derotation growth-friendly spine implant system according to claim 4, wherein each of the third fixing units comprises a third fixing bolt, a third locking bolt, and a third mounting part; the third mounting part is fixedly connected to the third fixing bolt; the third locking bolt is threadedly connected to the third mounting part; the third locking bolt presses the extending rod against an inner side wall of the third mounting part, and a friction force is applied to lock a relative position relationship between the extending rod and the third fixing unit.

9. The in vivo derotation growth-friendly spine implant system according to claim 5, wherein the second fixing end of the rod is provided with a connecting structure and an extending rod; the extending rod is connected to the rod through the connecting structure; one end of the extending rod away from the rod is provided with third fixing units; the third fixing units are separated from the extending rod and fixed on a side wall of the extending rod.

10. The in vivo derotation growth-friendly spine implant system according to claim 6, wherein the second fixing end of the rod is provided with a connecting structure and an extending rod; the extending rod is connected to the rod through the connecting structure; one end of the extending rod away from the rod is provided with third fixing units; the third fixing units are separated from the extending rod and fixed on a side wall of the extending rod.

11. The in vivo derotation growth-friendly spine implant system according to claim 7, wherein each of the third fixing units comprises a third fixing bolt, a third locking bolt, and a third mounting part; the third mounting part is fixedly connected to the third fixing bolt; the third locking bolt is threadedly connected to the third mounting part; the third locking bolt presses the extending rod against an inner side wall of the third mounting part, and a friction force is applied to lock a relative position relationship between the extending rod and the third fixing unit.

12. The in vivo derotation growth-friendly spine implant system according to claim 9, wherein each of the third fixing units comprises a third fixing bolt, a third locking bolt, and a third mounting part; the third mounting part is fixedly connected to the third fixing bolt; the third locking bolt is threadedly connected to the third mounting part; the third locking bolt presses the extending rod against an inner side wall of the third mounting part, and a friction force is applied to lock a relative position relationship between the extending rod and the third fixing unit.

13. The in vivo derotation growth-friendly spine implant system according to claim 1, wherein one end of the rod is provided with a connecting structure and an extending rod; the extending rod is connected to the rod through the connecting structure; one end of the extending rod away from the rod is provided with third fixing units; the third fixing units are separated from the extending rod and fixed on a side wall of the extending rod.

14. The in vivo derotation growth-friendly spine implant system according to claim 13, wherein each of the third fixing units comprises a third fixing bolt, a third locking bolt, and a third mounting part; the third mounting part is fixedly connected to the third fixing bolt; the third locking bolt is threadedly connected to the third mounting part; the third locking bolt presses the extending rod against an inner side wall of the third mounting part, and a friction force is applied to lock a relative position relationship between the extending rod and the third fixing unit.

15. The in vivo derotation growth-friendly spine implant system according to claim 1, wherein one end of the rod is provided with a connecting structure and an extending rod; the extending rod is connected to the rod through the connecting structure; one end of the extending rod away from the rod is provided with third fixing units; the third fixing units are separated from the extending rod and fixed on a side wall of the extending rod.

16. The in vivo derotation growth-friendly spine implant system according to claim 15, wherein each of the third fixing units comprises a third fixing bolt, a third locking bolt, and a third mounting part; the third mounting part is fixedly connected to the third fixing bolt; the third locking bolt is threadedly connected to the third mounting part; the third locking bolt presses the extending rod against an inner side wall of the third mounting part, and a friction force is applied to lock a relative position relationship between the extending rod and the third fixing unit.

17. The in vivo derotation growth-friendly spine implant system according to claim 1, wherein each of the third fixing units comprises a third fixing bolt, a third locking bolt, and a third mounting part; the third mounting part is fixedly connected to the third fixing bolt; the third locking bolt is threadedly connected to the third mounting part; the third locking bolt presses the extending rod against an inner side wall of the third mounting part, and a friction force is applied to lock a relative position relationship between the extending rod and the third fixing unit.

* * * * *